(12) United States Patent
Wan et al.

(10) Patent No.: US 9,477,814 B2
(45) Date of Patent: Oct. 25, 2016

(54) DISTRIBUTION OF AN IP-BASED MULTIMEDIA CHANNEL TO NON-IP ENABLED DEVICES

(71) Applicant: Broadcom Corporation, Irvine, CA (US)

(72) Inventors: Wade Keith Wan, Orange, CA (US); Rajesh Shankarrao Mamidwar, San Diego, CA (US)

(73) Assignee: Broadcom Corporation, Irvine, CA (US)

( * ) Notice: Subject to any disclaimer, the term of this patent is extended or adjusted under 35 U.S.C. 154(b) by 479 days.

(21) Appl. No.: 13/931,756

(22) Filed: Jun. 28, 2013

(65) Prior Publication Data

US 2014/0351383 A1  Nov. 27, 2014

Related U.S. Application Data

(60) Provisional application No. 61/826,473, filed on May 22, 2013.

(51) Int. Cl.

| | |
|---|---|
| *G06F 15/16* | (2006.01) |
| *G06F 19/00* | (2011.01) |
| *H04L 12/825* | (2013.01) |
| *H04L 29/06* | (2006.01) |
| *G06Q 10/08* | (2012.01) |
| *G06Q 50/22* | (2012.01) |

(52) U.S. Cl.
CPC ......... *G06F 19/3456* (2013.01); *G06Q 10/083* (2013.01); *G06Q 10/087* (2013.01); *G06Q 50/22* (2013.01); *H04L 47/25* (2013.01); *H04L 65/4084* (2013.01); *H04L 65/605* (2013.01)

(58) Field of Classification Search
None
See application file for complete search history.

(56) References Cited

U.S. PATENT DOCUMENTS

| | | | | |
|---|---|---|---|---|
| 6,466,543 | B1* | 10/2002 | Aoki | H04L 47/10 370/230 |
| 8,751,679 | B2* | 6/2014 | McHugh | H04N 21/23439 709/219 |
| 2004/0185864 | A1* | 9/2004 | Balachandran | H04W 28/22 455/452.2 |
| 2005/0047442 | A1* | 3/2005 | Volpe | H04L 12/2801 370/480 |
| 2009/0208006 | A1* | 8/2009 | Candelore | H04N 21/2347 380/200 |
| 2010/0205049 | A1* | 8/2010 | Long | G06Q 30/02 705/14.35 |

(Continued)

*Primary Examiner* — Joshua Joo
(74) *Attorney, Agent, or Firm* — McDermott Will & Emery LLP

(57) ABSTRACT

An apparatus and method for converting an IP-based multimedia channel and distributing the channel to a plurality of non-IP enabled devices based on the channel's popularity among the devices. The apparatus identifies a plurality of multimedia channels requested by a group of devices, and determines a data rate for providing each channel to the devices based on a popularity of each channel among the devices. The apparatus uses an adaptive bit rate (ABR) client to receive content segments for a respective one of the multimedia channels from an ABR server at a source data rate aligned with a determined data rate for providing the respective multimedia channel. The content segments are received at the source data rate, and converted by the apparatus to a continuous digital content stream. The apparatus then provides the continuous digital content stream to one or more of the devices at the determined data rate.

20 Claims, 4 Drawing Sheets

(56) References Cited

U.S. PATENT DOCUMENTS

| | | | |
|---|---|---|---|
| 2011/0310941 A1* | 12/2011 | Kenington | H04W 88/085 375/220 |
| 2012/0047230 A1* | 2/2012 | Begen | H04L 65/4092 709/219 |
| 2012/0311177 A1* | 12/2012 | Visharam | G06F 15/16 709/233 |
| 2013/0091249 A1* | 4/2013 | McHugh | H04N 21/23439 709/219 |
| 2013/0121261 A1* | 5/2013 | Yao | H04W 72/085 370/329 |
| 2013/0246578 A1* | 9/2013 | Moreman | H04L 67/2842 709/219 |
| 2014/0020037 A1* | 1/2014 | Hybertson | H04N 21/2365 725/109 |
| 2014/0095729 A1* | 4/2014 | Ma | H04L 65/608 709/231 |
| 2014/0237522 A1* | 8/2014 | Rothschild | H04N 21/236 725/88 |

* cited by examiner

DISTRIBUTION OF AN IP-BASED MULTIMEDIA CHANNEL TO NON-IP ENABLED DEVICES

The present application claims the benefit of priority under 35 U.S.C. §119 from U.S. Provisional Patent Application Ser. No. 61/826,473 entitled "Popularity-Based Distribution of an IP-Based Multimedia Channel to Non-IP Enabled Devices," filed on May 22, 2013, the disclosure of which is hereby incorporated by reference in its entirety for all purposes.

BACKGROUND

Hotels and other complexes may include one or more multi-tuner set top boxes (STBs) that provide cable television services to multiple local viewing devices (e.g., cable-ready televisions) in different rooms. Generally, these local viewing devices may include hardware for requesting channel feeds using quadrature amplitude modulation (QAM), but may not have the ability to consume IP-related streaming services. Accordingly, a multi-tuner STB may broadcast some channels to all devices, and provide other channels to some devices in response to individualized requests from those devices, all using QAM. The multi-tuner STB may further monitor what streams the devices are receiving.

SUMMARY

The subject technology provides a system and method for converting an IP-based multimedia channel and distributing the channel to a plurality of non-IP enabled devices based on the channel's popularity among the devices. The method may comprise identifying a plurality of multimedia channels requested by a group of devices, determining a data rate for providing each multimedia channel to the group of devices based on a popularity of each multimedia channel among the group of devices, selecting to receive content segments for a respective one of the multimedia channels from a content source at a source data rate aligned with a determined data rate for providing the respective multimedia channel, receiving the content segments from the content source at the source data rate, converting the content segments to a continuous digital content stream, and providing the continuous digital content stream to one or more devices in the group of devices at the determined data rate for providing the respective multimedia channel. Other aspects include corresponding systems, apparatus, and computer program products for implementation of the computer implemented method.

The previously described aspects and other aspects may include one or more of the following features. For example, the content segments may be received from the content source in a plurality of data packets over a network. The source data rate may be selected based on available bandwidth of the network. Converting the content segments may comprise removing a first encryption from the content segments and applying a second device-specific encryption to the continuous digital content stream for at least one of the devices in the group of devices. Providing the continuous digital content stream to one or more devices may comprise modulating a carrier signal with the continuous digital content stream, and providing the carrier signal to the one or more devices. The data rate for providing the respective multimedia channel may increase in response an increase in a number of devices requesting or viewing the multimedia channel relative to a number of devices requesting or viewing other channels, and the data rate for providing the respective multimedia channel may decrease in response a decrease in the number of devices requesting or viewing the multimedia channel relative to a number of devices requesting or viewing other channels.

Selecting to receive the content segments at a source data rate may comprise identifying a plurality of stream profiles advertised by an ABR server, each stream profile for receiving the content segments for the respective multimedia channel at a different data rate, and selecting a stream profile corresponding to the source data rate based on the determined data rate for providing the respective multimedia channel. In this regard, the stream profile may be selected based on a maximum source data rate that can be transcoded to the determined data rate without generating more than a predetermined amount of delay between when the content segments are received from the content source and converted to the continuous digital content stream.

Additionally or in the alternative, receiving the content segments from the content source at the source data rate may comprise sending one or more HTTP requests to the ABR server, each HTTP request being for a respective local content segment, and receiving the received source content segments from the ABR server according to the HTTP requests. Converting the content segments into a continuous digital content stream may comprise removing content headers from each of the content segments and coalescing the content segments. The method may further comprise monitoring available bandwidth for receiving content segments for the plurality of multimedia channels from the ABR server, and adjusting a determined data rate for providing one or more of the plurality of multimedia channels in response to a change in the available bandwidth.

In another aspect, a machine-readable medium may have instructions stored thereon that, when executed, cause a machine to perform a method. Accordingly, the method may comprise receiving a first plurality of content segments associated with a first multimedia channel and a second plurality of content segments associated with a second multimedia channel, each of the first and second pluralities of content segments being received at a data rate selected from a respective set of data rates advertised by the remote data source, converting the first and second plurality content segments to first and second continuous multimedia streams for a plurality of local viewing devices, determining a first number of local viewing devices that have requested to view or are viewing the first multimedia channel, and a second number of local viewing devices that have requested to view or are viewing the second multimedia channel, adjusting, based on the determining, a data rate for providing the first and second continuous multimedia stream to the plurality of local viewing devices, and providing the first and second continuous multimedia streams to the plurality of local viewing devices according to the adjusted data rate. Other aspects include corresponding systems, apparatus, and computer program products for implementation of the method.

In further aspects, a device may be configured to distribute IP-based multimedia channels to one or more non-IP enabled devices. In this regard, the device may be configured to identify a plurality of multimedia channels requested by a group of devices, determine a data rate for providing each multimedia channel based on a popularity of each multimedia channel among the group of devices, select to receive content segments for a respective one of the multimedia channels from an ABR server at a source data rate aligned with a determined data rate for providing the respective multimedia channel, receive, in a plurality of data packets over a network, the content segments from the content source at the ABR server, convert the content segments into a continuous digital content stream for transmission at the data rate for providing the respective multimedia channel, modulate a carrier signal with the continuous digital content stream, and provide the carrier signal to one or more devices in the group of devices It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

A detailed description will be made with reference to the accompanying drawings.

DETAILED DESCRIPTION

Figure 1:
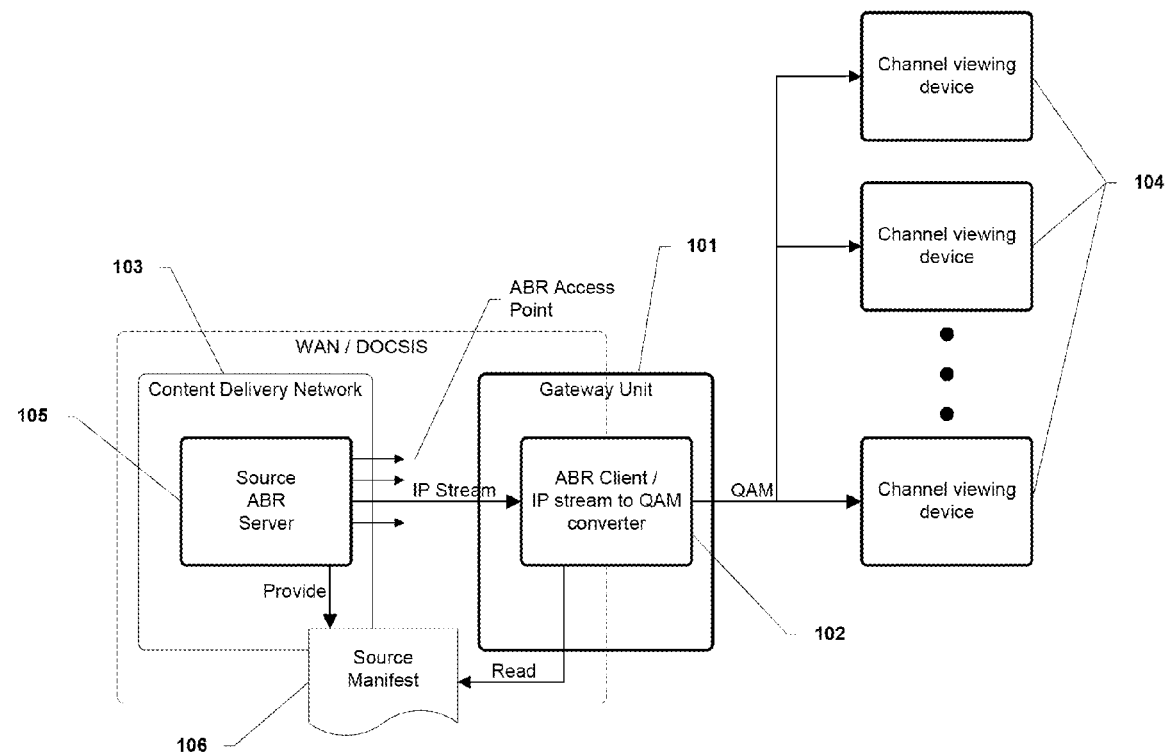
FIG. 1 depicts a component diagram of an example system for providing popularity-based distribution of an IP-based multimedia channel to non-IP enabled devices.

FIG. 1 depicts a component diagram of an example system for providing popularity-based distribution of an IP-based multimedia channel to non-IP enabled devices, in accordance with one or more implementations of the subject technology. A gateway unit 101 (e.g., a set-top box or unit, cable modem, DSL modem, or other device configured to receive digital multimedia content from a content source) is configured to consume and transmit digital multimedia content for one or more multimedia channels to one or more channel viewing devices (e.g., interactive television sets). Gateway unit 101, for example, may operate in connection with, or be configured as, a cable television headend that receives, processes, and distributes television signals to multiple cable television systems such as in a hotel or other facility that provides a cable television signal to multiple users. As will be described in further detail, gateway unit 101 is configured to receive streaming media ("IP streams") over an IP-based network (e.g., using TCP/IP, UDP, and the like) and convert the IP streams to digital multimedia content that may be rendered by non-IP enabled devices.

Gateway unit 101 generally includes a tuner for receiving traditional digital content (e.g., over QAM), and an ABR client 102 (e.g., embedded within gateway unit 101) for receiving IP streams from a content delivery network (CDN) 103. Gateway unit 101 may be implemented as, or include, a computing device (e.g., desktop, server, laptop, notebook, tablet computer) or other device connected to a network (e.g., a LAN, WAN, or the Internet) and configured to receive streaming media from an external source. Gateway unit 101 is configured to operate as an intermediary for requests from one or more local channel viewing devices 104 seeking a traditional signal for a multimedia channel that originates as an IP stream from CDN 103. Local channel viewing devices 104 may include, for example, a desktop, laptop, notebook, or tablet computer, smart phone, PDA, a television or other display device having a computer embedded within or attached thereto, or the like. Local channel viewing devices 104 may be connected to gateway unit 101 via coaxial cable, fiber optic, radio frequency, twisted pair, or other infrastructure suitable for audio visual transmission.

CDN 103 may be part of a cable TV system having a network infrastructure that utilizes Data Over Cable Service Interface Specification (DOCSIS) to provide high-speed data transfer to gateway unit 101 and other remotely connected devices. CDN 103 includes a (remote) source ABR server 105 or other multimedia server operably connected to unit 101 over a LAN, WAN, or the Internet. Source ABR server 105 provides streaming media content over HTTP. Source ABR server 105 receives digital content (e.g., a live television feed) from a content source and encodes the digital content into multiple streams, each segmented into small multi-second parts (e.g., between two (2) and ten (10) seconds in length) and provided at a different data rate (e.g., bit rate). Source ABR server 105 advertises the available source media streams of differing data rates by way of a source manifest file 106. Source manifest file 106 includes a stream profile for each source media stream and a playlist that describes the segments (e.g., the order and length of the segments) available from source ABR server 105.

When a local channel viewing device 104 requests to view a multimedia channel, ABR client 102 operably connects to source ABR server 105 (e.g., at an ABR access point of the associated network) and identifies source stream profiles advertised by source ABR server 105 for the channel, for example, by downloading and reading source manifest file 106. ABR client 102 selects a source stream profile for receiving a source media stream for the channel (e.g., including audio and/or video) from ABR server 105, and receives the source media stream as a plurality of data segments according to the selected profile.

ABR client 102 sends client HTTP uniform resource locator (URL) requests to ABR server 105 to receive corresponding local data segments from ABR server 105. Each client HTTP URL request requests transmission of a respective data segment at a selected one of the local ABR formats provided by the manifest file. Data segments are received from ABR server 105 according to the client HTTP requests, and the content segments are cached, desegmented, stripped of headers, and coalesced and converted to a continuous digital multimedia stream. In one or more implementations, the source media stream, including corresponding data segments, is transcoded by gateway unit 101. Transcoding may include, for example, changing a CODEC of the media stream, data rate of the media stream, or the like.

The continuous digital multimedia stream may then be transmitted to one or more local channel viewing devices 104 using a digital modulation scheme such as quadrature amplitude modulation (QAM). For a live source media stream, gateway unit 101, in connection with ABR client 102, may continuously convert the data segments for broadcast to multiple locally connected channel viewing devices 104. The conversion may occur in real time, or may be buffered such that one or more segments of data is converted at a time, and then provided to the locally connected devices.

ABR client 102 may select a source stream profile provided by source ABR server 105 based on one or more network conditions. For example, ABR client 102 may select a stream profile having the highest advertised bit rate available over an existing DOCSIS infrastructure and, if data-traffic congestion between ABR client 102 and source ABR server 105 is detected, ABR proxy 102 may select a new profile (advertised by manifest file 106) having a lower bit rate. Additionally, ABR client 102 may select the stream profile having the highest bit rate that the ABR client can convert to a non-IP based video stream (e.g., by transcoding).

In one or more implementations, ABR client 102 is configured to select a data profile for a multimedia channel based on how many local devices 104 have elected to receive the multimedia channel. Gateway unit 101 also adjusts the format (e.g., including the data rate and resolution) of the converted digital multimedia content based on the selected profile, available bandwidth between ABR client 102 and ABR server 105, and/or based on how many of the devices have elected to receive the content.

Gateway unit 101 is configured to determine the number of local channel viewing devices 104 that have requested to view, or are viewing, each available multimedia channel for a certain period of time, and to select a data profile for receiving each channel based on the popularity of the channel for all locally connected devices. Based on the number of devices identified to receive a particular channel, gateway unit 101 is configured to determine a resolution and corresponding data rate for providing the channel to the devices. For example, gateway 101 may attempt to increase resolution of a channel that has been requested by more than a predetermined number of local channel viewing devices 104. Accordingly, ABR client 102 is configured to retrieve data segments for each multimedia channel using a stream profile that is most closely aligned with the optimal data rate determined for devices that are to receive the multimedia channel, limited by available bandwidth of the connection to ABR server 105. Additionally or in the alternative, a stream profile may be selected based on an available data rate most efficient to transcode the source media stream to the optimal data rate determined for the locally connected devices.

If the source media stream for a particular multimedia channel is retrieved in a format that can be rendered by local channel viewing devices 104, and at a data rate that coincides with a data rate determined for those devices then gateway unit 101 may modulate the source media stream for distribution to the locally connected devices 104, for example, over QAM. If the source media stream is retrieved in a format that cannot be rendered by local channel viewing devices 104 (e.g., as data segments), and/or at a data rate that does not coincide with the data rate determined for those devices then gateway unit 101 may transcode the source media stream and modulate the converted multimedia content for distribution to the locally connected devices 104.

The number of local channel viewing devices 104 that are viewing a respective multimedia channel may vary at any time. With regard to a particular channel, gateway unit 101 is configured to determine the number of devices that have requested to view, or are viewing, the channel relative to devices that have requested other channels, and to adjust the data rate for providing digital content for the channel to the devices based on that determination. For example, gateway unit 101 may increase data rates (and resolution) for channels having a high popularity, while decreasing data rates (and resolution) for less popular channels.

The data rate of a digital multimedia content provided to locally connected devices 104 may further depend on the data rate that the corresponding source data segments are received from ABR server 105. Gateway unit 101 is configured to select a source data rate (e.g., from manifest file 106) based on the desired transmission data rate of the converted digital multimedia content. If a source data rate cannot be identified that is equal to or faster than the data rate for providing the converted digital content then gateway unit 101 may decrease the data rate for providing the digital multimedia content to locally connected devices to a data rate congruent with the speed at which the source stream may be received. Likewise, if the source stream is available at a higher data rate than the data rate used to provide the converted content to locally connected devices then gateway unit 101 may increase the data rate (and resolution) of the converted content.

In other aspects, gateway unit 101 may select a data rate profile for receiving a source media stream based network conditions between gateway unit 101 and ABR server 105, or between gateway unit 101 and the locally connected devices. Network conditions influencing profile selection may include, for example, a maximum data rate that ABR client 102 can receive the source media stream without producing substantial latency (e.g., delay) between receipt of the media stream and its subsequent conversion or transmission, or the highest data rate that gateway unit 101 can convert the source media stream to a signal suitable for the locally connected devices. Given the number of channels already being provided to locally connected channel viewing devices 104 and the bandwidth available from ABR server 105, gateway unit 101 may increase or decrease transmission data rates (and resolution) of digital content provided to those devices.

Figure 2:
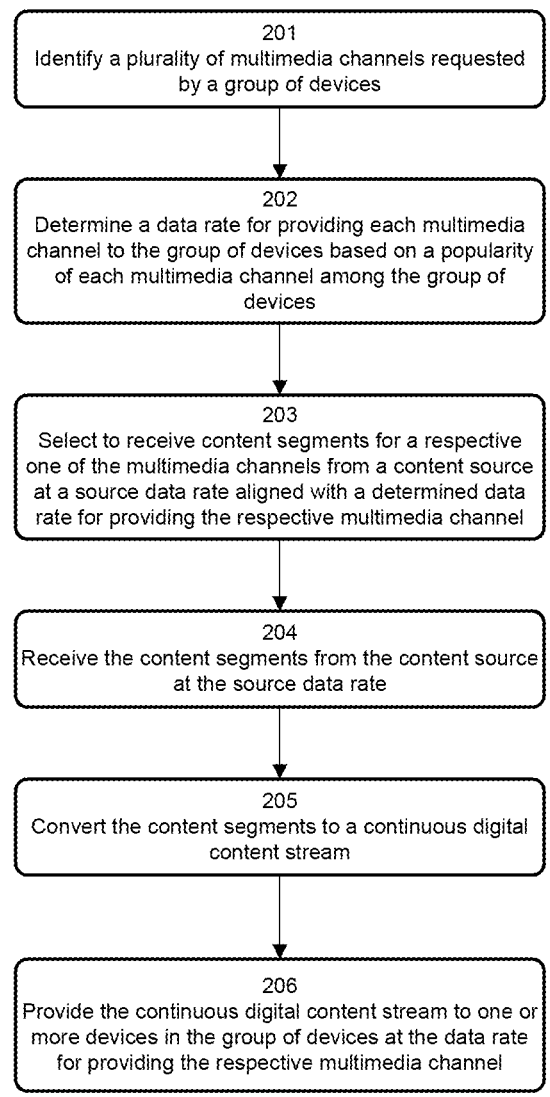
FIG. 2 is a flowchart illustrating an example process for converting an IP-based multimedia channel and distributing the channel to a plurality of non-IP enabled devices based on the channel's popularity among the devices.

FIG. 2 is a flowchart illustrating an example process for converting an IP-based multimedia channel and distributing the channel to a plurality of non-IP enabled devices based on the channel's popularity among the devices, in accordance with one or more implementations of the subject technology. The blocks of FIG. 2 do not need to be performed in the order shown. It is understood that the depicted order is an illustration of one or more example approaches, and are not meant to be limited to the specific order or hierarchy presented. The blocks may be rearranged, and/or or more of the blocks may be performed simultaneously.

According to one or more implementations, one or more blocks of FIG. 2 may be executed by gateway unit 101 or other computing device of the subject technology. Similarly, a non-transitory machine-readable medium may include machine-executable instructions thereon that, when executed by a computer or machine, perform the blocks of FIG. 2. Accordingly, the blocks of FIG. 2 may be performed within the context of distributing a multimedia channel received using a network protocol to a non-IP enabled device (e.g., a television or other display device).

According to FIG. 2, a plurality of multimedia channels requested by a group of devices are identified (201). Gateway unit 101 may be connected to multiple viewing devices. For example, gateway 101 may be part of or located at a cable headend, and receive television signals for distribution over a cable television system to multiple cable-ready televisions. Accordingly, gateway unit 101 is configured to monitor requests to view multimedia channels (e.g., a television station) from the connected devices, and identify which devices are requesting each channel. Likewise, gateway unit 101 is configured to determine how many devices have requested each available channel.

A data rate for providing each multimedia channel to the group of devices is determined (202) based on a popularity of each multimedia channel among the group of devices. Gateway unit 101 is configured to provide highly requested channels at a higher resolution and audio/video quality. The use of the term "data rate," unless otherwise indicated, is intended to be used synonymously for audio and/or video display resolution, format, quality and/or bit rate, in that an increase or decrease in data rate will produce a corresponding increase or decrease in audio and/or video display resolution, format, quality and/or bit rate of multimedia content distributed at the data rate.

Accordingly, the data rate for providing the respective multimedia channel (e.g., the quality or resolution) may increase in response an increase in a number of devices requesting or viewing the multimedia channel relative to a number of devices requesting or viewing other channels. Likewise, the data rate for providing the respective multimedia channel may decrease in response to a decrease in the number of devices requesting or viewing the multimedia channel relative to a number of devices requesting or viewing other channels. Additionally, or in the alternative, the data rate may increase or decrease in response to the total available bandwidth (e.g., between gateway unit 101 and source ABR server 105, or between gateway unit and the locally connected devices 104) and the bandwidth required to deliver all channels being requested by locally connected devices 104. In one or more implementations, the data rate for providing the respective multimedia channel may decrease in response to a decrease in available network bandwidth or a decrease in memory or other resources available to ABR client 102 (e.g., embedded memory) for receiving, converting, and/or transmitting digital content.

Content segments for a respective one of the multimedia channels are selected (303) to be received from a content source at a source data rate aligned with a determined data rate for providing the respective multimedia channel. For example, gateway unit 101 may identify a plurality of stream profiles advertised by ABR server 105. Each stream profile advertised by ABR server 105 may be for receiving the content segments for the respective multimedia channel at a different data rate. Gateway unit 101 may select a stream profile corresponding to the source data rate based on the determined data rate for providing the respective multimedia channel. Accordingly, the source data rate may be a data rate equal or equivalent to the data rate determined for providing the channel. As described previously, the source data rate may also be selected, for example, based on available bandwidth of the network. In one or more implementations, the stream profile may be selected based on a maximum source data rate that can be transcoded to the determined data rate without generating more than a predetermined amount of delay between when the content segments are received from the content source and converted to the continuous digital content stream.

In various aspects, gateway unit 101 may monitor available bandwidth for receiving content segments for all multimedia channels from ABR server 105, and adjust a determined data rate for providing one or more of the plurality of multimedia channels in response to a change in the available bandwidth. For example, if the available bandwidth decreases then gateway unit 101 may decrease the data rate for providing one or more multimedia channels. Selection of which channels for decreased data rate may be based on their popularity with respect to other channels, with less popular channels being selected. In this manner, gateway unit 101 can continue to provide a higher quality signal to viewers of more popular channels, thereby maintaining overall viewer satisfaction. As bandwidth is restored or increases, gateway unit 101 may increase the data rate for these channels, for example, in order of popularity.

With continued reference to FIG. 2, the content segments for the respective multimedia channel are received (204) from the content source at the source data rate. As described previously, ABR server 105 may be a content source for providing one or more multimedia channels as IP streams from a CDN over a network (e.g., a WAN, LAN, or the Internet). Accordingly, content segments may be received by gateway unit 101 from ABR server 105 in a plurality of corresponding data packets over the network. ABR server 105 may provide a playlist for a multimedia channel that describes the content segments for the channel, and provides a URL for retrieving each segment. Accordingly, gateway unit 101 may send one or more HTTP requests to ABR server 105, with each HTTP request being for a respective local content segment. ABR server 105 returns the content segments to gateway unit 101 according to the HTTP requests.

In one or more aspects, gateway unit 101 may receive first plurality of content segments associated with a first multimedia channel and a second plurality of content segments associated with a second multimedia channel. In these aspects, gateway unit 101 may select a source data rate from each of a respective set of data rates advertised by ABR server 105 (e.g., in separate manifest files 106). Each of the first and second pluralities of content segments may then be received at their respective data rates selected by gateway unit 101.

The content segments for the respective multimedia channel are converted (205) to a continuous digital content stream. The content segments are converted for transmission at the determined data rate for providing the multimedia channel. This process may be accomplished by, or as part of, an ongoing transcoding of content segments received from ABR server 105. For example, converting the content segments into a continuous digital content stream may include removing content headers from each of the content segments and coalescing the content segments, for example, in a memory cache. The bare segments may be reassembled in correct order and decoded to produce a video signal that may be compatible with local viewing devices 104. Accordingly, the content segments may be transcoded into digital content having a resolution corresponding to the determined data rate for providing the respective multimedia channel.

The continuous digital content stream is provided (206) to one or more devices in the group of devices at the data rate for providing the respective multimedia channel. Providing the digital content stream may include, for example, modulating (e.g., using QAM) a carrier signal with the continuous digital content stream, and then providing the carrier signal to the one or more devices (e.g., over coaxial cable). In one or more implementations, the digital content stream may be provided as an encrypted transport stream, encrypted in connection with a digital rights management (DRM) scheme provided by software operating on or in connection with gateway unit 101.

With limited bandwidth available from the content delivery network or headend, the number of simultaneous channels provided to locally connected devices 104 may contribute to determining which ABR data rate to select. For example, a better quality data rate may be selected in response to determining that there are a smaller number of viewed channels. Additionally, the number of locally connected devices 104 that are viewing a specific channel may be used to determine the selected ABR data rate. For example, if there are a hundred or so devices viewing an NFL game and only a single device viewing local public TV station then gateway unit 101 may select a higher data rate for the NFL game to deliver a better quality experience to a wider audience.

Figure 3:
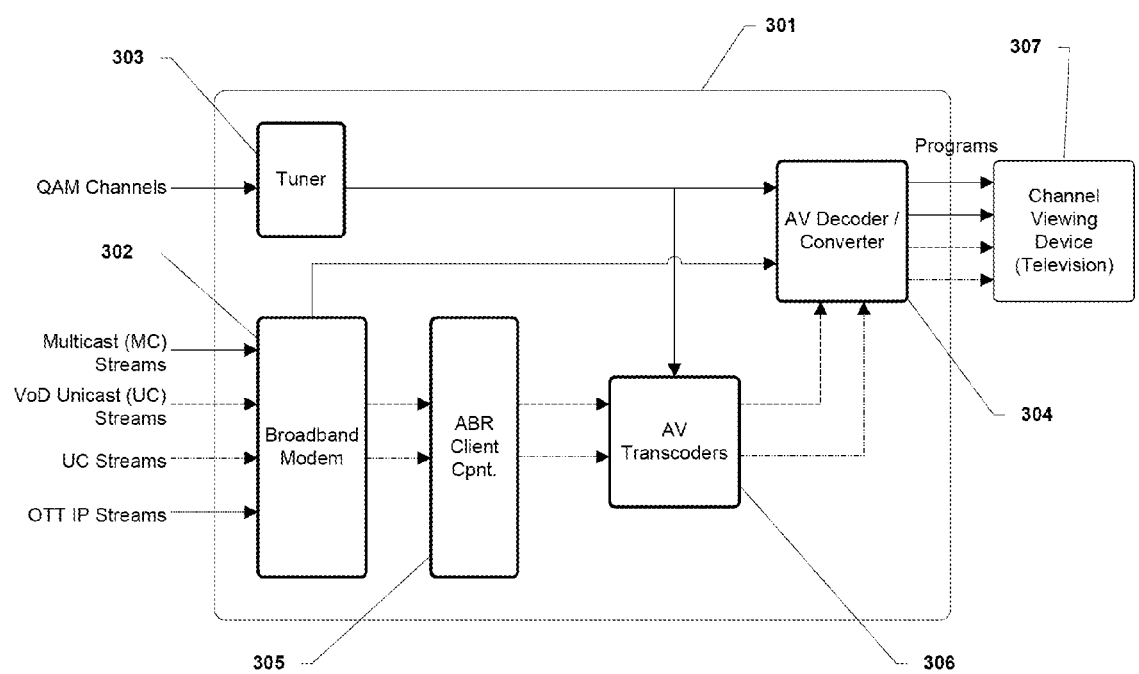
FIG. 3 is a diagram illustrating an example gateway unit for providing popularity-based distribution of an IP-based multimedia channel to non-IP enabled devices.

FIG. 3 is a diagram illustrating an example gateway unit 301 for providing popularity-based distribution of an IP-based multimedia channel to non-IP enabled devices, in accordance with one or more implementations of the subject technology. Gateway unit 301 includes a broadband modem 302 (e.g., a cable modem), a multi-tuner 303 (e.g., a QAM (quadrature amplitude modulation) tuner or ATSC (Advanced Television Systems Committee) tuner), an audio/video decoder and converter 304, an ABR client component 305, and one or more audio/video transcoders 306.

Over-the-air (OTA) digital channels may be received via QAM by tuner 303 and decoded by audio/video decoder/converter 304 for broadcast to one or more locally connected channel viewing devices 307 (e.g., a television or other display device). Broadband modem 302 is connected to a content delivery network. Broadband model 302 may act as a data pipe for ABR client component 305, which selects an appropriate data rate for receiving a stream based on network conditions. ABR client component 305 is configured to receive IP streams from an ABR server and provides the streams for decoding by decoder 304 or for transcoding operations by transcoders 306. Additionally or in the alternative, ABR client component 305 may be configured to remove encryption from received content. In this regard, converter 304 may be configured to receive the content from ABR client component 305 and to apply device-specific encryption (e.g., digital rights management (DRM) or other access control) before the content is transmitted to locally connected viewing devices 307. Gateway unit 301 is further configured with one or more processors (see FIG. 4) and/or software that coordinate receipt of QAM signals and streaming media, decoding and/or transcoding operations, and distribution to the locally connected viewing devices 307.

Gateway unit 301 is configured to provide multimedia channels on demand to locally connected viewing devices 307, and to monitor the total number of watched channels. On providing a channel for viewing, the receiving device is identified. Accordingly, gateway unit 101 identifies which multimedia channels are requested by the active group of locally connected devices. Based on the popularity of each currently provided channel, gateway determines which channels are to be provided at a higher or lower data rate. For a respective channel, ABR client component 305 selects to receive content segments for the channel from an ABR server at a source data rate aligned with a determined data rate for providing the channel. Content segments are received from the ABR server in a plurality of data packets over the network, and converted into a continuous digital content stream by decoder and converter 304 for transmission at the determined data rate for the channel. In one or more aspects, the content segments may be transcoded to a different format by transcoders 406 before the conversion. Gateway unit 401 then modulates a carrier signal with the continuous digital content stream, and provides the carrier signal to one or more devices identified to receive the channel.

Figure 4:
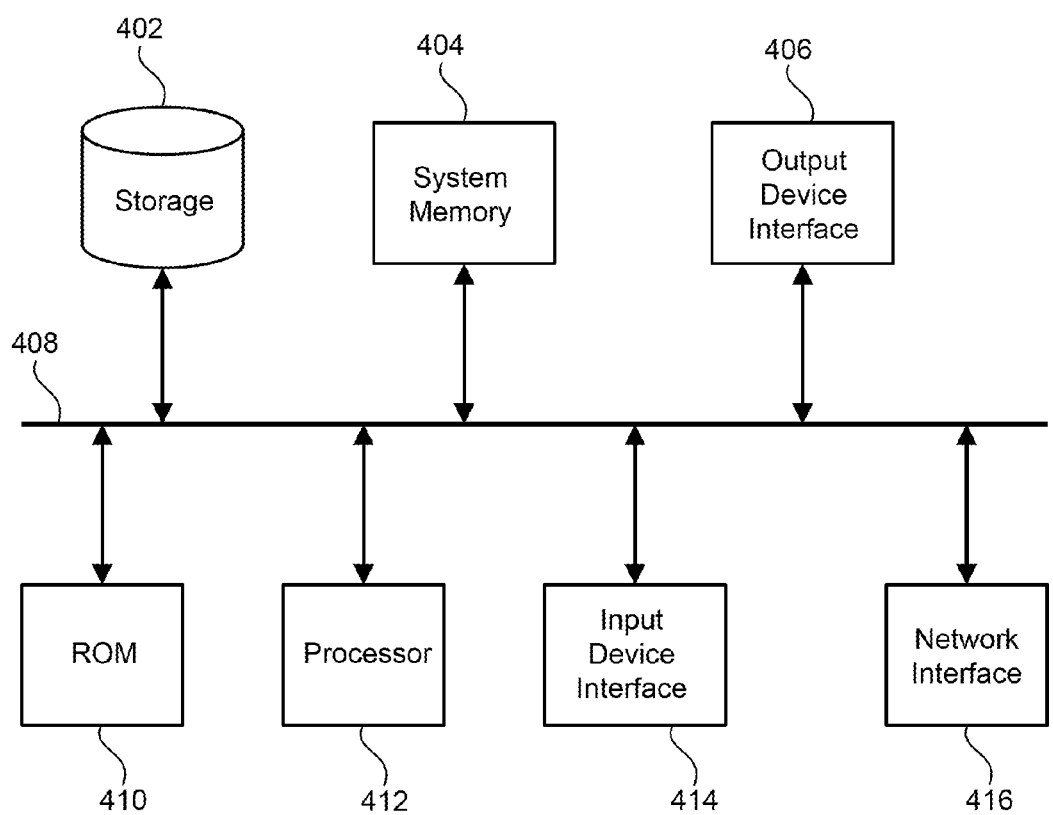
FIG. 4 is a diagram illustrating an example electronic system for use in connection with providing popularity-based distribution of an IP-based multimedia channel to non-IP enabled devices, including a processor and other related components.

FIG. 4 is a diagram illustrating an example electronic system 400 for use in connection with providing popularity-based distribution of an IP-based multimedia channel to non-IP enabled devices, including a processor and other related components, in accordance with one or more implementations of the subject technology. Electronic system 400, for example, is representative of the computing hardware embedded within, or for providing functional operation of, the previously described devices, including gateway unit 101, 301, local channel viewing device 104, 307, and the like. In one or more aspects, electronic system 400 may be a desktop computer, a laptop computer, a tablet computer, a server, a switch, a router, a base station, a receiver, a phone, a personal digital assistant (PDA), or generally any electronic device that transmits signals over a network. Such an electronic system includes various types of computer readable media and interfaces for various other types of computer readable media. Electronic system 400 includes bus 408, processing unit(s) 412, system memory 404, read-only memory (ROM) 410, permanent storage device 402, input device interface 414, output device interface 406, and network interface 416, or subsets and variations thereof.

Bus 408 collectively represents all system, peripheral, and chipset buses that communicatively connect the numerous internal devices of electronic system 400. In one or more implementations, bus 408 communicatively connects processing unit(s) 412 with ROM 410, system memory 404, and permanent storage device 402. From these various memory units, processing unit(s) 412 retrieves instructions to execute and data to process in order to execute the processes of the subject disclosure. The processing unit(s) can be a single processor or a multi-core processor in different implementations.

ROM 410 stores static data and instructions that are needed by processing unit(s) 412 and other modules of the electronic system. Permanent storage device 402, on the other hand, is a read-and-write memory device. This device is a non-volatile memory unit that stores instructions and data even when electronic system 400 is off. One or more implementations of the subject disclosure use a mass-storage device (such as a magnetic or optical disk and its corresponding disk drive) as permanent storage device 402.

Other implementations use a removable storage device (such as a floppy disk, flash drive, and its corresponding disk drive) as permanent storage device 402. Like permanent storage device 402, system memory 404 is a read-and-write memory device. However, unlike storage device 402, system memory 404 is a volatile read-and-write memory, such as random access memory. System memory 404 stores any of the instructions and data that processing unit(s) 412 needs at runtime. In one or more implementations, the processes of the subject disclosure are stored in system memory 404, permanent storage device 402, and/or ROM 410. From these various memory units, processing unit(s) 412 retrieves instructions to execute and data to process in order to execute the processes of one or more implementations.

Bus 408 also connects to input and output device interfaces 414 and 406. Input device interface 414 enables a user to communicate information and select commands to the electronic system. Input devices used with input device interface 414 include, for example, alphanumeric keyboards and pointing devices (also called "cursor control devices"). Output device interface 406 enables, for example, the display of images generated by electronic system 400. Output devices used with output device interface 406 include, for example, printers and display devices, such as a liquid crystal display (LCD), a light emitting diode (LED) display, an organic light emitting diode (OLED) display, a flexible display, a flat panel display, a solid state display, a projector, or any other device for outputting information. One or more implementations may include devices that function as both input and output devices, such as a touchscreen. In these implementations, feedback provided to a user or device can be any form of sensory feedback, such as visual feedback, auditory feedback, or tactile feedback; and input from the user or device can be received in any form, including acoustic, speech, or tactile input.

As shown in FIG. 4, bus 408 also couples electronic system 400 to a network (not shown) through network interface 416. In this manner, the computer can be a part of a network of computers (such as a local area network ("LAN"), a wide area network ("WAN"), or an Intranet, or a network of networks, such as the Internet. Any or all components of electronic system 400 can be used in conjunction with the subject disclosure.

Implementations within the scope of the present disclosure can be partially or entirely realized using a tangible computer-readable storage medium (or multiple tangible computer-readable storage media of one or more types) encoding one or more instructions. The tangible computer-readable storage medium also can be non-transitory in nature.

The computer-readable storage medium can be any storage medium that can be read, written, or otherwise accessed by a general purpose or special purpose computing device, including any processing electronics and/or processing circuitry capable of executing instructions. For example, without limitation, the computer-readable medium can include any volatile semiconductor memory, such as RAM, DRAM, SRAM, T-RAM, Z-RAM, and TTRAM. The computer-readable medium also can include any non-volatile semiconductor memory, such as ROM, PROM, EPROM, EEPROM, NVRAM, flash, nvSRAM, FeRAM, FeTRAM, MRAM, PRAM, CBRAM, SONOS, RRAM, NRAM, racetrack memory, FJG, and Millipede memory.

Further, the computer-readable storage medium can include any non-semiconductor memory, such as optical disk storage, magnetic disk storage, magnetic tape, other magnetic storage devices, or any other medium capable of storing one or more instructions. In some implementations, the tangible computer-readable storage medium can be directly coupled to a computing device, while in other implementations, the tangible computer-readable storage medium can be indirectly coupled to a computing device, e.g., via one or more wired connections, one or more wireless connections, or any combination thereof.

Instructions can be directly executable or can be used to develop executable instructions. For example, instructions can be realized as executable or non-executable machine code or as instructions in a high-level language that can be compiled to produce executable or non-executable machine code. Further, instructions also can be realized as or can include data. Computer-executable instructions also can be organized in any format, including routines, subroutines, programs, data structures, objects, modules, applications, applets, functions, etc. As recognized by those of skill in the art, details including, but not limited to, the number, structure, sequence, and organization of instructions can vary significantly without varying the underlying logic, function, processing, and output.

In one or more implementations, a computer program product (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

While the above discussion primarily refers to microprocessor or multi-core processors that execute software, one or more implementations are performed by one or more integrated circuits, such as application specific integrated circuits (ASICs) or field programmable gate arrays (FPGAs). In one or more implementations, such integrated circuits execute instructions that are stored on the circuit itself.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon design preferences, it is understood that the specific order or hierarchy of blocks in the processes may be rearranged, or that all illustrated blocks be performed. Any of the blocks may be performed simultaneously. In one or more implementations, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

As used in this specification and any claims of this application, the terms "base station", "receiver", "computer", "server", "processor", and "memory" all refer to electronic or other technological devices. These terms exclude people or groups of people. For the purposes of the specification, the terms "display" or "displaying" means displaying on an electronic device.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The predicate words "configured to", "operable to", and "programmed to" do not imply any particular tangible or intangible modification of a subject, but, rather, are intended to be used interchangeably. In one or more implementations, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as an "aspect" may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as a "configuration" may refer to one or more configurations and vice versa.

The word "exemplary" is used herein to mean "serving as an example, instance, or illustration." Any embodiment described herein as "exemplary" or as an "example" is not necessarily to be construed as preferred or advantageous over other embodiments. Furthermore, to the extent that the term "include," "have," or the like is used in the description or the claims, such term is intended to be inclusive in a manner similar to the term "comprise" as "comprise" is interpreted when employed as a transitional word in a claim.

All structural and functional equivalents to the elements of the various aspects described throughout this disclosure that are known or later come to be known to those of ordinary skill in the art are expressly incorporated herein by reference and are intended to be encompassed by the claims. No claim element is to be construed under the provisions of 35 U.S.C. §112, sixth paragraph, unless the element is expressly recited using the phrase "means for" or, in the case of a method claim, the element is recited using the phrase "step for."

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

What is claimed is:

1. A method for distributing an IP-based multimedia channel to a plurality of non-IP enabled devices, comprising:
   identifying, by a device, a plurality of multimedia channels requested by a group of devices; determining a data rate for providing each multimedia channel to the group of devices based on a popularity of each multimedia channel among the group of devices;
   aligning, by the device, the determined data rate for a respective one of the multimedia channels with one of a plurality of source data rates provided over a network by a content source, wherein the aligning comprises selecting the one of the plurality of source data rates provided by the content source that is closest to the determined data rate for the respective one of the multimedia channels;
   selecting to receive, by the device and over the network, content segments for the respective one of the multimedia channels from the content source at the one of the plurality of source data rates aligned with the determined data rate for providing the respective multimedia channel;
   receiving the content segments from the content source over the network at the one of the plurality of source data rates;
   converting, by the device, the content segments at the one of the plurality of source data rates to a continuous digital content stream; and
   providing the continuous digital content stream to one or more devices in the group of devices at the determined data rate for providing the respective multimedia channel.

2. The method of claim 1, wherein providing the continuous digital content stream to one or more devices comprises:
   modulating a carrier signal with the continuous digital content stream; and
   providing the carrier signal to the one or more devices.

3. The method of claim 1, wherein the data rate for providing the respective one of the multimedia channels increases in response an increase in a number of devices requesting or viewing the respective one of the multimedia channels relative to a number of devices requesting or viewing other multimedia channels of the multimedia channels, and the data rate for providing the respective one of the multimedia channels decreases in response a decrease in the number of devices requesting or viewing the respective one of the multimedia channels relative to a number of devices requesting or viewing other multimedia channels of the multimedia channels.

4. The method of claim 1, selecting to receive the content segments at the one of the plurality of source data rates comprises:
   identifying a plurality of stream profiles advertised by an adaptive bit rate (ABR) server, each stream profile for receiving the content segments for the respective multimedia channel at a different data rate; and
   selecting one of the plurality of stream profiles corresponding to the one of the plurality of source data rates based on the determined data rate for providing the respective multimedia channel.

5. The method of claim 4, wherein the one of the plurality of stream profiles is selected based on a maximum source data rate that is transcodable to the determined data rate without generating more than a predetermined amount of delay between when the content segments are received from the content source and converted to the continuous digital content stream.

6. The method of claim 4, wherein receiving the content segments from the content source at the one of the plurality of source data rates comprises:
   sending one or more HTTP requests to the ABR server, each HTTP request being for a respective content segment; and
   receiving the respective content segments from the ABR server according to the HTTP requests.

7. The method of claim 4, wherein converting the content segments into the continuous digital content stream comprises:
   removing content headers from each of the content segments and coalescing the content segments.

8. The method of claim 4, further comprising:
   monitoring available bandwidth for receiving content segments for the plurality of multimedia channels from the ABR server; and
   adjusting the determined data rate for providing one or more of the plurality of multimedia channels in response to a change in the available bandwidth.

9. The method of claim 1, wherein converting the content segments comprises removing an encryption from the content segments and applying a device- specific encryption to the continuous digital content stream for at least one of the devices in the group of devices.

10. The method of claim 9, wherein the one of the plurality of source data rates is selected based at least in part on available bandwidth of the network.

11. A computer program product comprising instructions stored in a non-transitory computer-readable storage medium, the instructions comprising:
   instructions to receive a first plurality of content segments associated with a first multimedia channel and a second plurality of content segments associated with a second multimedia channel from an adaptive bit rate (ABR) server, each of the first and second pluralities of content segments being received at a data rate selected from a respective set of data rates advertised by a remote data source;
   instructions to convert the first and second plurality content segments to first and second continuous multimedia streams for a plurality of local viewing devices;
   instructions to determine a first number of local viewing devices that have requested to view or are viewing the first multimedia channel, and a second number of local viewing devices that have requested to view or are viewing the second multimedia channel;
   instructions to adjust, based at least in part on the determining, respective data rates for providing the first and second continuous multimedia streams to the plurality of local viewing devices;
   instructions to monitor available bandwidth for receiving the first and second pluralities of content segments from the ABR server and to adjust the respective data rates for providing the first and second continuous multimedia stream in response to a monitored change in the available bandwidth; and
   instructions to provide the first and second continuous multimedia streams to the plurality of local viewing devices according to the respective adjusted data rates.

12. The computer program product of claim 11, wherein the instructions to convert the first and second pluralities of content segments to first and second continuous multimedia streams comprise:
   instructions to remove for each of the pluralities of content segments, content headers from the content segments and coalescing the content segments.

13. The computer program product of claim 12, wherein the instructions to provide the first and second continuous multimedia streams comprise:
   instructions to modulate one or more carrier signals with the first and second continuous multimedia streams; and
   instructions to provide the one or more carrier signals to the plurality of local viewing devices.

14. The computer program product of claim 11, wherein the first and second pluralities of content segments are received from the ABR server, the computer program product further comprising:
   instructions to select a first stream profile for the first multimedia channel from a plurality of stream profiles advertised by a first manifest file, each stream profile corresponding to a different data rate for receiving the first plurality of content segments; and
   instructions to select a second stream profile for the second multimedia channel from a plurality of stream profiles advertised by a second manifest file, each stream profile corresponding to a different data rate for receiving the second plurality of content segments.

15. The computer program product of claim 14, wherein the instructions to receive the first and second pluralities of content segments comprise:
   instructions to send one or more HTTP requests to the ABR server, each HTTP request being for a respective content segment; and
   instructions to receive the respective content segments from the ABR server according to the HTTP requests.

16. The computer program product of claim 15, further comprising: instructions to receive each of the respective content segments from the ABR server according to a corresponding playlist provided by the ABR server.

17. The computer program product of claim 14, wherein the instructions to adjust, based at least on the determining, the respective data rates for providing the first and second continuous multimedia streams to the plurality of local viewing devices further comprises:
   instructions to adjust, based at least on the determining and a total amount of shared bandwidth available to the plurality of local viewing devices, the respective data rates for providing the first and second continuous multimedia streams to the plurality of local viewing devices.

18. The computer program product of claim 11, wherein the instructions to adjust comprise instructions to determine the respective data rates for providing each multimedia channel based on a popularity of the first and second multimedia channels among the plurality of local viewing devices.

19. The computer program product of claim 11, wherein the first and second pluralities of content segments are received from the remote data source in a plurality of data packets over a network.

20. A device comprising:
   at least one processor circuit configured to:
      identify a plurality of multimedia channels requested by a group of devices;
      determine a data rate for providing each multimedia channel based on a popularity of each multimedia channel among the group of devices;
      select to receive content segments for a respective one of the multimedia channels from an adaptive bit rate (ABR) server at a source data rate that is aligned with the determined data rate for providing the respective multimedia channel, the source data rate not exceeding a maximum source data rate that is transcodable to the determined data rate without more than a predetermined amount of delay between when the content segments are received from the ABR server and converted to a continuous digital content stream;

receive, in a plurality of data packets over a network, the content segments from a content source at the ABR server;

convert the content segments into the continuous digital content stream for transmission at the determined data rate for providing the respective multimedia channel;

modulate a carrier signal with the continuous digital content stream; and provide the carrier signal to one or more devices in the group of devices.

* * * * *